United States Patent
Vogt et al.

(10) Patent No.: US 8,606,370 B2
(45) Date of Patent: Dec. 10, 2013

(54) CONNECTION ELEMENT FOR CONDUCTION COIL

(75) Inventors: Christoph Vogt, St. Paul, MN (US); Lena Lewandrowski, Mainhausen (DE); Stefan Schibli, Frankfurt am Main (DE); Christiane Leitold, Woelfersheim (DE); René Richter, Babenhausen (DE)

(73) Assignee: W. C. Heraeus GmbH, Hanau (DE)

( * ) Notice: Subject to any disclaimer, the term of this patent is extended or adjusted under 35 U.S.C. 154(b) by 177 days.

(21) Appl. No.: 12/837,976

(22) Filed: Jul. 16, 2010

(65) Prior Publication Data

US 2011/0015709 A1    Jan. 20, 2011

(30) Foreign Application Priority Data

Jul. 17, 2009   (DE) .................. 10 2009 033 767

(51) Int. Cl.
*A61N 1/05*    (2006.01)
(52) U.S. Cl.
USPC .......................................... 607/122; 607/115
(58) Field of Classification Search
USPC ................................ 607/115–128
See application file for complete search history.

(56) References Cited

U.S. PATENT DOCUMENTS

| | | | |
|---|---|---|---|
| 4,538,623 A * | 9/1985 | Proctor et al. | 607/122 |
| 4,566,467 A * | 1/1986 | DeHaan | 607/116 |
| 5,241,957 A | 9/1993 | Camps et al. | |
| 5,593,433 A | 1/1997 | Spehr et al. | |
| 5,676,694 A * | 10/1997 | Boser et al. | 607/122 |
| 6,505,081 B1 | 1/2003 | Das | |
| 6,526,321 B1 | 2/2003 | Spehr | |
| 7,191,017 B1 | 3/2007 | Koop et al. | |
| 2004/0064174 A1 | 4/2004 | Belden | |
| 2005/0004642 A1 | 1/2005 | Shoberg | |
| 2011/0015710 A1 | 1/2011 | Vogt et al. | |
| 2011/0015711 A1 | 1/2011 | Vogt et al. | |

FOREIGN PATENT DOCUMENTS

| | | |
|---|---|---|
| DE | 69214156 | 4/1997 |
| DE | 202004008492 | 9/2004 |
| DE | 102007009716 | 9/2008 |
| WO | 2006104432 | 10/2006 |

OTHER PUBLICATIONS

Office Action for U.S. Appl. No. 12/837,995 mailed Dec. 16, 2011 (15 pages).
Office Action for U.S. Appl. No. 12/837,983 mailed May 2, 2012 (16 pages).
Final Office Action for U.S. Appl. No. 12/837,995 mailed May 22, 2012 (17 pages).

* cited by examiner

*Primary Examiner* — Rex R Holmes
(74) *Attorney, Agent, or Firm* — Dicke, Billig & Czaja, PLLC

(57) ABSTRACT

One aspect is a medical electrode system including a conduction coil and a stimulation electrode. The stimulation electrode encompasses a base body having a top area and an end area. The system is characterized in that the conduction coil encompasses a connection element. The connection element is thermally shrink-fitted onto the end area.

13 Claims, 5 Drawing Sheets

CONNECTION ELEMENT FOR CONDUCTION COIL

CROSS-REFERENCE TO RELATED APPLICATIONS

This Utility Patent Application claims priority to German Patent Application No. DE 10 2009 033 767.9, filed on Jul. 17, 2009, which is incorporated herein by reference.

This Patent Application is also related to patent application Ser. No. 12/837,983 filed Jul. 16, 2010, entitled "CRIMP CONNECTION BETWEEN STIMULATION ELECTRODE AND CONDUCTION COIL"; and patent application Ser. No. 12/837,995 filed Jul. 16, 2010 entitled "CONNECTION BETWEEN STIMULATION ELECTRODE AND CONDUCTION COIL".

BACKGROUND

One aspect relates to a medical electrode system having a conduction coil and a stimulation electrode, wherein the stimulation electrode encompasses a base body having a top area and an end area. One aspect furthermore relates to a method for connecting a conduction coil to a stimulation electrode.

Stimulation electrodes as well as medical electrode systems are described in DE 10 2007 009 716 A1. Such stimulation electrodes must be connected to electric feed lines—also referred to as conduction coils. As a rule, the stimulation electrodes thereby consist of a high-melting metal, the feed lines from a metal having a lower melting temperature. These two components are often connected to one another by means of laser welding. However, due to the differences of the two metals, which are to be connected to one another, it is possible the required mechanical stability or electric conductivity is not reached. Tears, which among others are caused by forming intermetallic phases or by the solidification behavior after the welding, can appear in the weld zone. Due to different melting temperatures, the fusion is partially insufficient. As a rule, such errors cannot be determined in a non-destructive manner, which can lead to considerable problems in the production or quality control, respectively.

For these and other reasons there is a need for the present invention.

SUMMARY

One aspect relates to a medical electrode system having conduction coil and a stimulation electrode, wherein the stimulation electrode encompasses a base body having a top area and an end area. Provision is made according to one embodiment for the conduction coil to encompass a connection element, wherein the connection element is thermally shrink-fitted onto the end area.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further advantages, features and details of embodiments result from the dependent claims and from the following description, in which a plurality of exemplary embodiments are described in detail with reference to the drawings. The features mentioned in the claims and in the description can thereby in each case be important for embodiments, either alone or in any combination.

DETAILED DESCRIPTION

Figure 1:
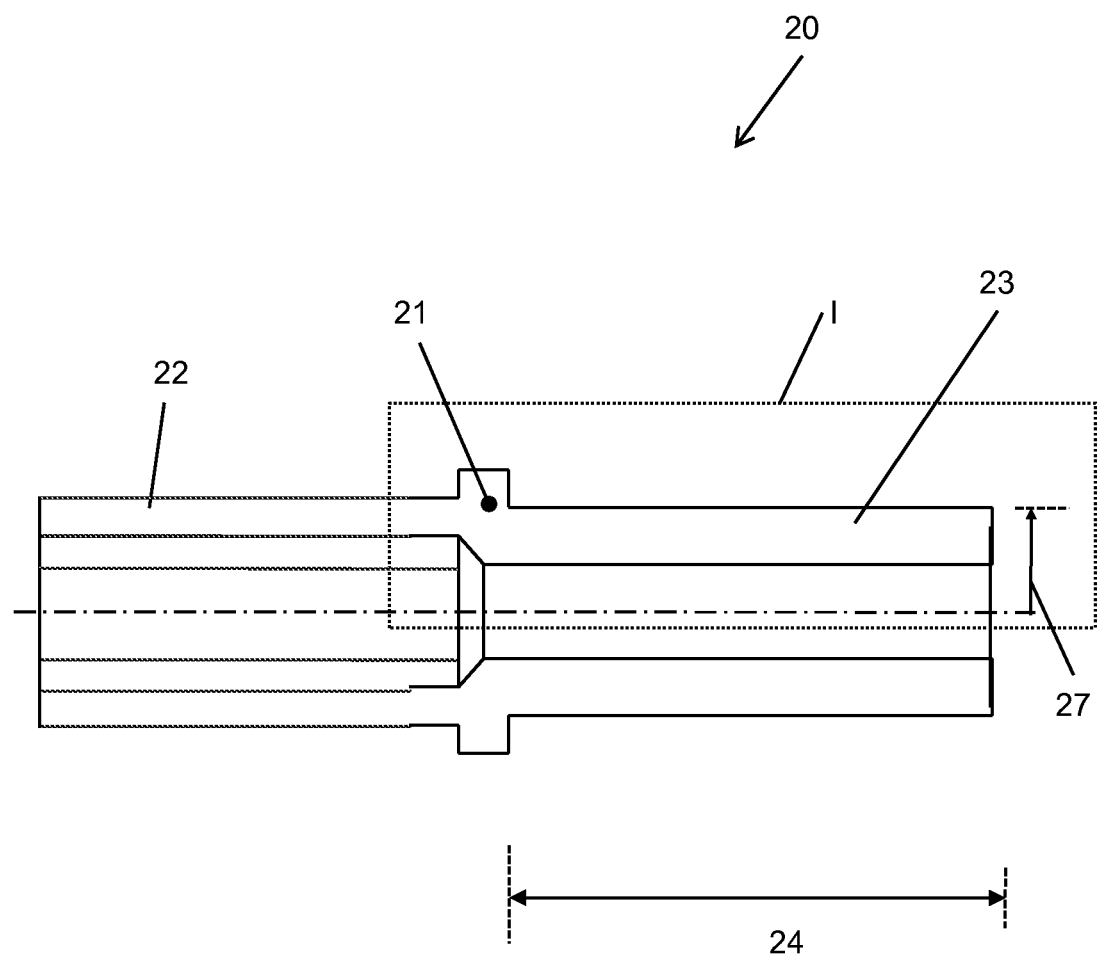
FIG. 1 illustrates a stimulation electrode according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

According to one aspect of one embodiment, a medical electrode system is created, in the case of which the mentioned disadvantages are avoided, and in one embodiment, a connection is created between the stimulation electrode and the conduction coil, which is stable and durable in the long run.

A medical electrode system and a method for connecting a conduction coil to a stimulation electrode are proposed. Features and details, which are described in context with the medical electrode system, thereby also apply in context with the method and vice versa in each case.

For the medical electrode system according to one embodiment, provision is made for the conduction coil to encompass a connection element, wherein the connection element is thermally shrink-fitted onto the end area.

One aspect of one embodiment is that the conduction coil and the stimulation electrode of the medical electrode system are connected in that the connection element is thermally shrink-fitted onto the end area. This shrink-fitting leads to a non-positive and/or positive connection between the conduction coil and the stimulation electrode. The above-mentioned disadvantages, which appear, for example, when the melting temperatures of the conduction coil and of the stimulation electrode differ to a high extent, can thus be prevented.

In the context of one embodiment, the term "thermally shrink-fitting" is to be understood such that the characteristic of a material, the expansion with increasing heat, is adopted. For instance, the connection element can be heated and can thus expand its geometric shape. In this heated state, the connection element can then be pushed onto the end area. After a thermal cooling of the connection element, the geometric shape thereof shrinks such that a non-positive and/or positive connection is created between the connection element and the end area.

In the context of one embodiment, the description also includes that the end area of the stimulation electrode is cooled to a high degree and thus reduces its geometric size. Subsequently, the connection element can then also be pushed across the end area. In response to a heating of the end area to the temperature of the connection element, for example, room temperature, a non-positive and/or positive connection also takes place between the connection element and the end area.

A first embodiment of the medical electrode system is characterized in that the connection element is connected to the conduction area on the end side. As will be explained in more detail, the connection element can either be assembled from a plurality of loops of the conduction coil or can be a separate element, which is connected to the loops of the conduction area. In the described embodiment, the connection element thus forms the distal end of the conduction coil. Signals of a medically implantable device, such as a pace maker, pass through the conduction area of the conduction coil, so as to subsequently reach into the connection element. From there, the transition from the conduction coil into the stimulation electrode takes place and subsequently into the cardiac tissue via the active surface. The connection of the connection element to the conduction area on the end side ensures a simple and rapid assembly of the conduction coil on the stimulation electrode.

A further embodiment is characterized in that an inner diameter of the connection element is adapted to an outer diameter of the end area, so as to thermally shrink-fit the conduction coil onto the stimulation electrode in a connection situation. So as to establish a non-positive and/or positive connection between the connection element and the end area, the inner diameter of the connection element—in response to the same temperature—should not be greater than the outer diameter of the end area. In the event that the connection element is now heated thermally, the inner diameter increases, so that it becomes greater than the outer diameter of the end area. The connection element can then be pushed onto the end area. In response to the subsequent cooling, the inner diameter of the connection element shrinks back again to its initial size and thus leads to a non-positive and/or positive connection between the two elements of the medical electrode system.

The medical electrode system serves as electric connection between an electrotherapeutic implantable apparatus, which can be a neuro stimulator, a pace maker, a defibrillator or another suitable electrotherapeutic implantable apparatus and the area in the body, which is to be treated. These areas in the body can be of the most varying type, such as a heart, for example. The medical electrode system cannot only serve to transfer therapeutic pulses, but also to transfer body and measuring signals to the implant, so that suitable therapy can specifically be performed in answer to the body signals.

The medical electrode system according to one embodiment encompasses an elongate body having a proximal and a distal end. Provision is made on the proximal end for a connection to an electrotherapeutic implantable apparatus. This can be a pace maker, a cardioverter/defibrillator or another suitable heart rhythm apparatus. A fastening device for securely fastening the stimulation electrode to the cardiac tissue is located at the distal end. On the one hand, this can be a so-called passive fixation, which is embodied in an anchor-shaped manner and which can hook into the myocardial muscle. On the other hand, it can be an active fixation, which can actively be screwed into the cardiac tissue by means of a helical screw, which can be screwed in. This helically embodied stimulation electrode can also be electrically conductive and can thus act as additional electrically active surface. The area of the medical electrode system, which is located between the proximal and distal end, can furthermore be sealed and insulated from the environment. The outer surface is coated here with silicon or a similar synthetic material. In the distal area of the medical electrode system, the sealed and insulated outer surface is interrupted by at least one electrically active surface. These electrically active surfaces are areas of the stimulation electrode, which can provide for a stimulation of the above-mentioned type in the atrium of the heart, for example.

In the context of one embodiment, the term stimulation electrode does not refer to the transition point of the electric energy according to physical definition, but also refers to the technical line of electric conductor and can, if need be, also include an encasing insulation as well as all further functional elements, which are fixedly connected to the line. For clarification purposes, the section of the stimulation electrode, which actually operates in the physical sense and which include the transition point of the electric energy, will be referred to hereinbelow as "electrically active surface."

The conduction coil encompasses individual or a plurality of wires, which form loops, which are arranged in a helical manner. The loops of the conduction coil can be embodied as multiple coils, wherein the individual loops can be located coaxially and/or parallel to one another and can encompass the same outer diameter. The loops of the conduction coil can also be wound in a multifilar manner and can be provided with an electric insulation.

One embodiment of the medical electrode system is characterized in that the two parts conduction coil and stimulation electrode, which are directly connected to one another, are formed from metals having a different melting temperature from the group consisting of the elements Pt, Pd, Ag, Au, Nb, Ta, Ti, Zr, W, V, Hf, Mo, Co, Cr, Ni, Ir, Re, Ru as well as from alloys on the basis of at least one of these elements, for example, that the metal of the conduction coil encompasses a lower melting temperature than the metal of the stimulation electrode.

It is known in the state of the art to connect stimulation electrodes and conduction coil to one another by means of welding, for example, laser welding. However, difficulties arise due to the differences, for example, in the melting temperatures of the two materials, which are to be connected to one another. For instance, tears can appear in the melting zone, which are caused by the different solidification behavior of the two used materials. The medical electrode system according to one embodiment lends itself so as not to have to do without the use of materials having very different melting temperatures for the conduction coil on the one hand and for the stimulation electrode on the other hand.

By means of the described embodiment of the conduction coil and of the stimulation electrode of the medical electrode system, the conduction coil on the one hand and the stimulation electrode on the other hand can in each case be formed from metals, which encompass very different melting temperatures. In one embodiment alternative, the difference of the melting temperatures of the two parts—conduction coil and stimulation electrode—is at least 1000° C., and in one embodiment at least 1500° C. Another embodiment alternative is characterized in that the melting temperature of the higher melting material is at least 2400° C., and in one embodiment at least 2800° C.

In an embodiment alternative, the conduction coil can encompass MP-35, for instance, and the stimulation electrode can encompass tantalum. MP35 (approximately 35 weight % of nickel, approximately 35 weight % of cobalt, approximately 20 weight % of chromium and approximately 10 weight % of molybdenum) has a melting point of approximately 1400° C. Tantalum has a melting point of 2996° C., so that the temperature difference of the melting temperatures of the two materials is greater than 1500° C. In a further example, the stimulation electrode can be formed from Ta-10W, including a melting point of 3040° C. The conduction coil can be formed from a core jacket wire (DTF), wherein the core consists of tantalum and the jacket consists of MP35N. Here, the difference of the melting temperatures of the two parts is above 1500° C. as well. In a further example, a niobium-containing stimulation electrode can be used as stimulation electrode. In the event that a conduction coil of MP35N is used, the difference of the melting temperatures is more than 1000° C., because the melting temperature of niobium is 2468° C.

Due to the fact that according to one embodiment a welding of the conduction coil to the stimulation electrode by means of material engagement is not carried out, but a non-positive and/or positive connection by means of thermal shrink-fitting, the conduction coil and the stimulation electrode can encompass metals including very different melting temperatures. By means of the thermal shrink-fitting, it is possible to transfer forces via the connection between conduction coil and stimulation electrode, as it is otherwise only possible with connection between similar metals by means of material engagement. These surprising results of a plurality of measurements confirm that the medical electrode system, which is embodied according to one embodiment, is particularly suitable as pace maker electrode, because even a plurality of load changes and movements do not lead to a destruction or dissolution of the connection between stimulation electrode and conduction coil.

A further embodiment is characterized in that the stimulation electrode of the medical electrode system encompasses at least one from the group of tantalum, niobium, titanium or platinum, and in one embodiment that the stimulation electrode encompasses a TaNbW alloy. The mentioned group of metals is characterized by a particular biocompatibility, as well as by a high electric conductivity. In one embodiment alternative, the stimulation electrode encompasses a tantalum-niobium-tungsten alloy (TaNbW alloy including 10 weight % of niobium and 7.5 weight % of tungsten) or consists thereof. The tantalum-niobium-tungsten alloy turned out to be preferred in one embodiment as base material for the base body and the tantalum oxide layer, because it encompasses a high tensile strength and a specific capacitance, which is almost twice as high. A reduction of the losses in response to the transfer of stimulation pulses is thus possible.

The stimulation electrode of the medical electrode system according to one embodiment can encompass the valve metal tantalum or can consist thereof. A stimulation electrode, which is embodied in such a manner, can be provided with a tantalum oxide layer by means of high voltage pulses. The method used for this is also referred to as plasma-electrolytic oxidation (PEO) and is described in more detail in WO 2006/104432 A1 for niobium. In the disclosed method, a porous structure of the corresponding metal oxide is generated on the surface of the stimulation electrode by means of plasma-electrolytic oxidation. It thereby turned out to be an anomaly that the porous structure encompasses pores, which are considerably larger than it is known from the current state of the art, thus resulting in a stimulation electrode having an electrically conductive base body, wherein the base body encompasses in particular tantalum and the base body is at least partially covered with a porous tantalum oxide layer, which is anodically applied by means of high voltage pulses.

A further embodiment of the medical electrode system according to one embodiment is characterized in that the conduction coil and/or the connection element encompass at least one from the group MP-35, MP-35N and DFT. In this alternative, the conduction coil can encompass a "drawn filled tube" (DFT). Such DFTs encompass two components, a bio-resistant, biocompatible and non-toxic component and a component of a material having a low electric resistance. For the most part, the bio-resistant, biocompatible and non-toxic component is embodied to protect the component of a material having a low electric resistance. Platinum, iridium or an alloy of these two materials is preferred in one embodiment. In a further embodiment, the core including a low electric resistance consists of a material from the vanadium group ($5^{th}$ subgroup of the periodic table of the elements) or from the copper group ($1^{st}$ subgroup of the periodic table of the elements). In one embodiment, the core of the DFT wire consists of tantalum (Ta), niobium (Nb) or gold (Au). The conduction coil and/or the connection element can furthermore encompass MP-35 and/or MP-35N (MP35N is a protected mark of SPS Technologies, Inc.). MP35N substantially encompasses approximately 35 weight % of nickel, approximately 35 weight % of cobalt, approximately 20 weight % of chromium and approximately 10 weight % of molybdenum.

In one embodiment, to attain an advantageous mass ratio for the conduction coil, which forms a defibrillation electrode, provision can be made for an outer diameter of this conduction coil to be at least five, six or seven times the diameter of the coil-forming wire or an intermediate value thereof. This leads to a flexible conduction coil including an advantageous outer dimension, which provides for a sufficiently large field intensity distribution in response to the defibrillation and thus for a relatively low shock energy.

A further embodiment of the medical electrode system is characterized in that the end area and/or the connection area are embodied in a cylindrical manner. This embodiment makes it possible to simply slide the heated connection element onto the end area and simultaneously a large contact area between both, which ensures the positive and/or non-positive connection after cooling. In one embodiment, the connection element can be a one-piece and tube-like element. In one embodiment, connection element and conduction area are made from the same material, so that a connection by means of material engagement between both can be established in a simple manner. The connection element can consequently encompass all of the materials, which have been listed above for the conduction coil. The connection element, which is embodied in a tube-like and/or cylindrical manner, can encompass an internal bore, so as to be slid over the end area. A length of the connection element is matched to a length of the end area. The connection element can thus cover the entire end area. It is also possible for the connection element to be shorter than the end area, so that further coils of the conduction area come to rest on the end area. This has the effect that the connection by means of material engagement between connection element and conduction area is not subjected to possible shearing and bending forces, which can appear when the medical electrode system is implanted into a heart, for instance. These shearing and bending forces act on the conduction coil only where the conduction area separates from the end area of the stimulation electrode.

In an alternative embodiment alternative, the connection element consists of a plurality of loops of the conduction coil, which are connected by means of material engagement. The conduction area and the connection element are consequently both formed from loops of the helical conduction coil. Those loops, which are arranged on the distal end of the conduction coil, can be connected by means of welding, for example, laser welding, and can thus form the connection element. In this embodiment alternative, a separate element, which is connected to the loops of the conduction coil, is not necessary. Instead, these loops form the connection element itself by means of the connection by means of material engagement. Due to the fact that there is a material uniformity between the connection element and the conduction area here as well, the above-described disadvantages in response to the connection of different materials do not arise. The thermal shrink-fitting then makes it possible for the connection element to enter into a non-positive and/or positive connection with the stimulation electrode.

One embodiment also relates to a method for connecting a conduction coil to a stimulation electrode. According to one embodiment, a method according includes:

a. at least one from the group of an inner diameter of a connection element of the conduction coil and of an outer diameter of an end area of the stimulation electrode is changed by means of a thermal impact, b. the connection element is slid onto the end area and c. the connection element is shrink-fitted onto the end area by reaching a thermal balance.

It goes without saying that features and details, which have been disclosed in context with the medical electrode system, also apply in context with the disclosed method and vice versa in each case. The anomaly of the method according to one embodiment lies in that a connection by material engagement is not aimed at between the conduction coil and the stimulation electrode. Instead, a thermal impact, a heating of the conduction coil, changes the outer diameter thereof such that the connection element can be slid across the end area of the stimulation electrode. A thermal balance, for example, a thermal cooling of the connection element, takes place thereafter, whereby the geometric dimensions of said connection element shrink. This shrinking leads to a non-positive and/or positive connection between the conduction coil and the stimulation electrode. This method has turned out to be preferred in one embodiment when conduction coil and stimulation electrode are in each case made up of materials, which encompass very different melting points.

A further method step is characterized in that a plurality of loops of the conduction coil are welded with one another at least area by area for forming the connection element. One embodiment of the conduction coil of the medical electrode system is characterized in that the connection element includes one or a plurality of loops of the conduction coil. The loops are arranged in a helical manner so as to form the conduction coil. In an embodiment, a plurality of at least two loops is connected by means of material engagements, for instance by means of welding. The connection of a plurality of loops of the conduction coil in the connection area by means of material engagement further prevents the respective wire ends and/or loop ends of the conduction coil to unwind when in use.

A stimulation electrode 20 according to one embodiment is illustrated in FIG. 1. The stimulation electrode 20 encompasses a cylindrically embodied base body 21. The base body 21 encompasses a top area 22 and an end area 23. The illustration of the top area 22 is only schematic. The top area 22 encompasses an active surface, which is used to transfer and/or to sense electric pulses. The base body 21 furthermore encompasses the end area 23, which is also embodied cylindrically. A borehole runs in the interior of the base body 21, so that the stimulation electrode is embodied in a tube-like manner.

In the illustrated exemplary embodiment, the end area 23 as well as the top area is embodied cylindrically. This is to serve only to clarify one embodiment herein. Embodiments are not limited such that the end area 23 or the top area 22 are embodied accordingly. A dam-like structure is arranged on the stimulation electrode between end area 23 and top area 22. Said dam-like structure simultaneously serves as stop for the connection element 70, which will be described below.

The starting point for one embodiment is the fact that tears can appear in the melting zones in response to the connection by means of material engagement—such as laser welding, for instance—of metals including very different melting temperatures. These tears can then lead to the weakening of the connection between stimulation electrode and conduction coil. The connection between stimulation electrode and conduction coil can break later at these weak points and can thus endanger a possible patient.

To overcome that, one embodiment describes a medical electrode system in the case of which the conduction coil encompasses a connection element, which is thermally shrink-fitted onto the end area 23 of the stimulation electrode 20. To make this possible, it turned out to be advantageous in one embodiment when the end area 23 is embodied in a cylindrical manner and encompasses a constant diameter 27. A simple sliding of the heated connection element is thus possible.

FIGS. 2 to 6 illustrate in each case possible embodiments of the conduction coil 40 for the electrode system 10 according to one embodiment. A double section along the longitudinal and diagonal axis through the conduction coil is in each case drawn in. Only a fourth of the helically wound loops 43 of the conduction coil 40 can thus be seen. The conduction coil 40 encompasses a conduction area 41. Electric pulses can be transmitted by an implantable medical apparatus, such as a pace maker, for instance, to the stimulation electrode 20 through the loops 43 of the conduction area 41. In the illustrated exemplary embodiment, 2 loops 43 are joined by means of a welding point 80. These loops 43 form the connection element 70. The inner radius 72 of the connection element 70 is chosen such that it is not greater than the outer radius 27 of the end area 23 of the stimulation electrode 20 when both parts encompass the same temperature. The connection element 70 can be slid across the end area 23 only after a heating and a resulting thermal expansion thereof. In the event that a cooling of the connection element 70 then takes place, the geometry, and thus also the inner radius 72, decreases. This leads to a non-positive and/or positive connection between the stimulation electrode 20 and the conduction coil 40. The inner radius 72 of the connection element 70 should thus be adapted to the outer radius 27 of the end area 23 such that the conduction coil can be thermally shrink-fitted onto the stimulation electrode in a connection situation.

Figure 2:
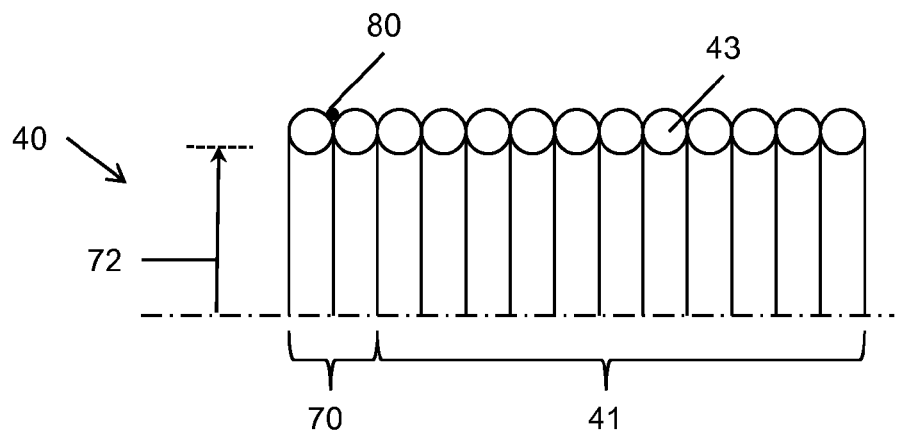
FIG. 2 illustrates a conduction coil according to one embodiment of the medical electrode system.
Figure 3:
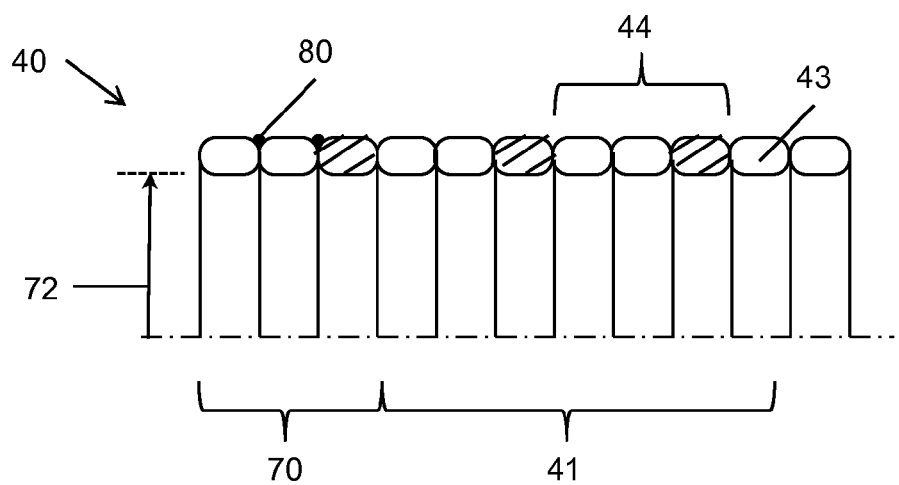
FIG. 3 illustrates a further conduction coil.

FIG. 2 clarifies that the conduction coil 40 consists of individual loops 43, which encompass a circular cross section. To form the conduction coil 40 and/or the loops 43 of the conduction coil 40, a wire is wound helically. It is also possible for the loops 43 of the conduction coil to encompass a rectangular cross section, as is clarified in FIG. 3. This cross section can be generated, for example, by pulling or crushing a wire, which is otherwise provided with a round cross section. FIG. 3 is to furthermore clarify that the conduction coil 40 can be formed by a plurality of wires. In this case, three helical parts are screwed into one another such that a conduction coil 40 is created, in the case of which the individual loops 43 of the helical parts are arranged next to one another. This is to be clarified by means of shading, which illustrates one of the three helical parts. The three helical parts, which form the conduction coil 40, thereby form loop packets 44, which include three loops 43 in each case.

Figure 4:
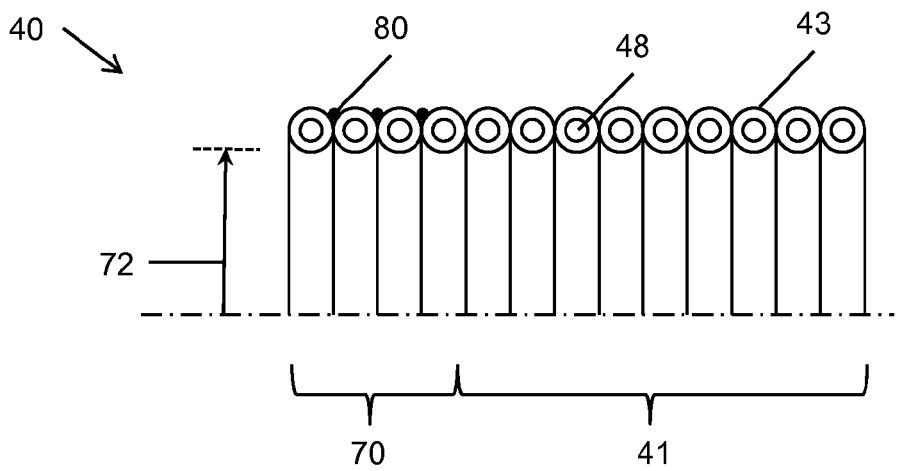
FIG. 4 illustrates an alternative embodiment of the conduction coil.
Figure 6:
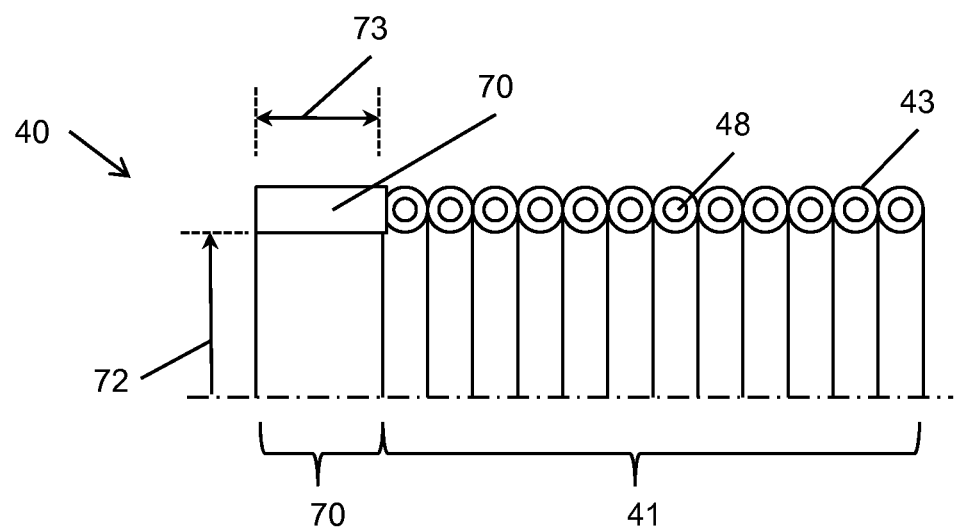
FIG. 6 illustrates a further embodiment of a conduction coil.

FIG. 4 illustrates a further embodiment of the conduction coil 40. The used conduction coil 40 is a so-called "drawn filled tube" (DFT). A DFT thereby encompasses two components: a bio-resistant, non-toxic component and a component consisting of a material including a low, electric resistance. Generally, the bio-compatible component forms a cover over the component including the low electric resistance. In FIGS. 4 and 6, this is to be clarified in that each of the loops 43 encompasses a core 48, which is to represent the component including the low electric resistance. The cross section of the individual loops 43 can thereby vary.

Figure 5:
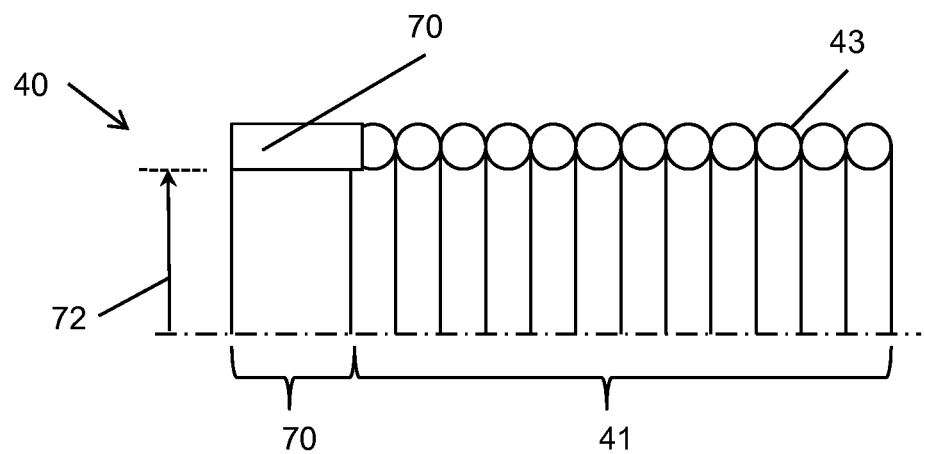
FIG. 5 illustrates a conduction coil having a one-piece connection element.

In FIGS. 2 to 4, the connection element was in each case formed by means of a connection of a plurality of loops 43 of the conduction coil 40 by means of material engagement. An alternative embodiment is illustrated in FIGS. 5 and 6. In this embodiment alternative, the connection element 70 is embodied in one piece and in a tube-like manner. That connection element 70 is thus not formed from individual loops of the conduction coil, but is attached thereto only on the end side by means of material engagement. This can take place, for example, by means of a welding, such as, a laser welding. In one embodiment, connection elements 70 and the loops 43 of the conduction area 41 are made from the same material. It is thus prevented that tears or other deficiencies could appear in the area of the connection by means of material engagement between the connection element 70. FIG. 6 illustrates a further embodiment of a conduction coil 40 according to one embodiment. The connection element 70 is also embodied herein in one piece and in a tube-like manner. Contrary to FIG. 5, DTF wires are used as loops 43 of the conduction area 41.

Figure 7:
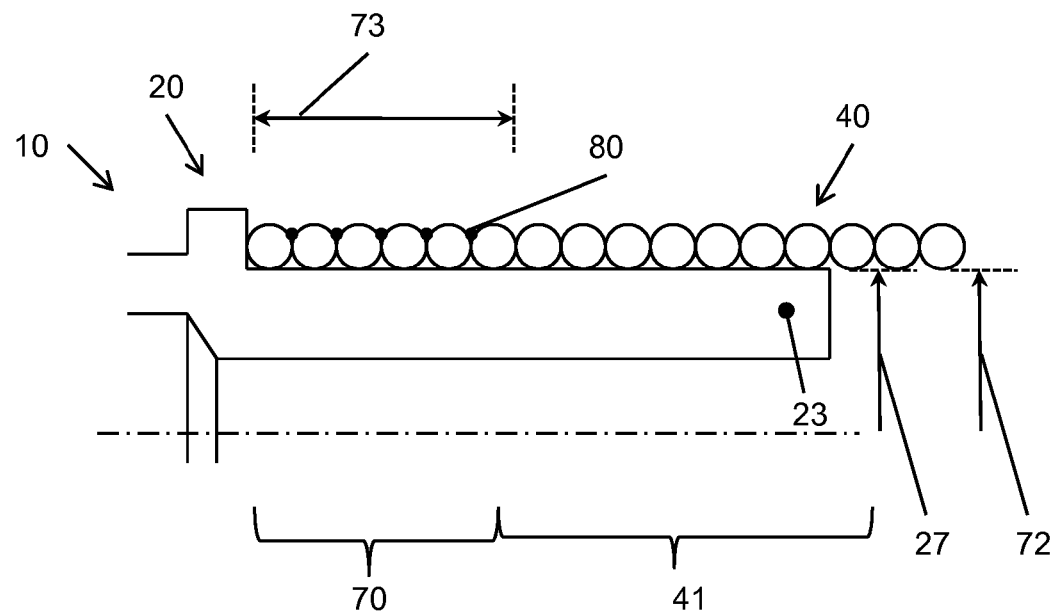
FIG. 7 illustrates the medical electrode system having a stimulation electrode and a conduction coil.
Figure 8:
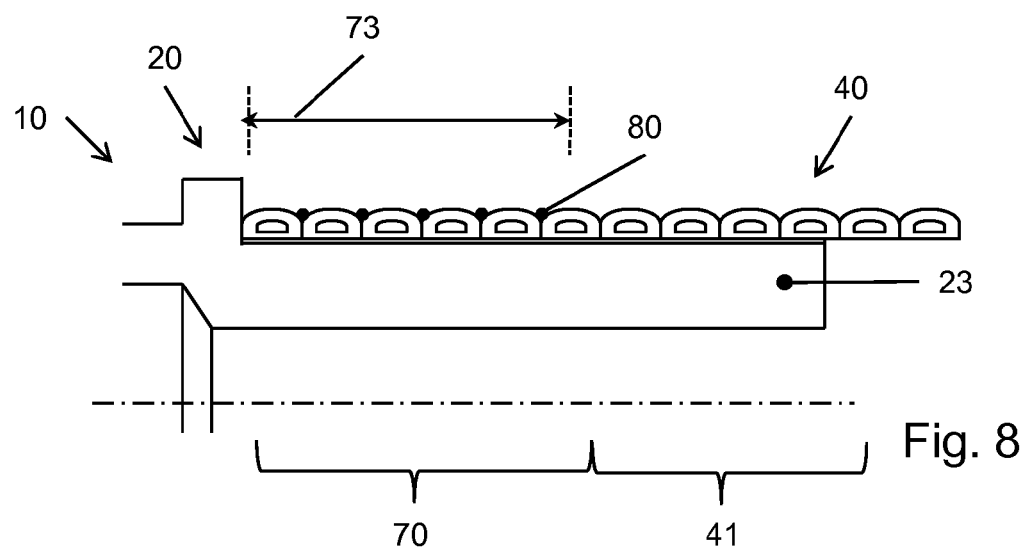
FIG. 8 illustrates a further embodiment of the medical electrode system.
Figure 9:
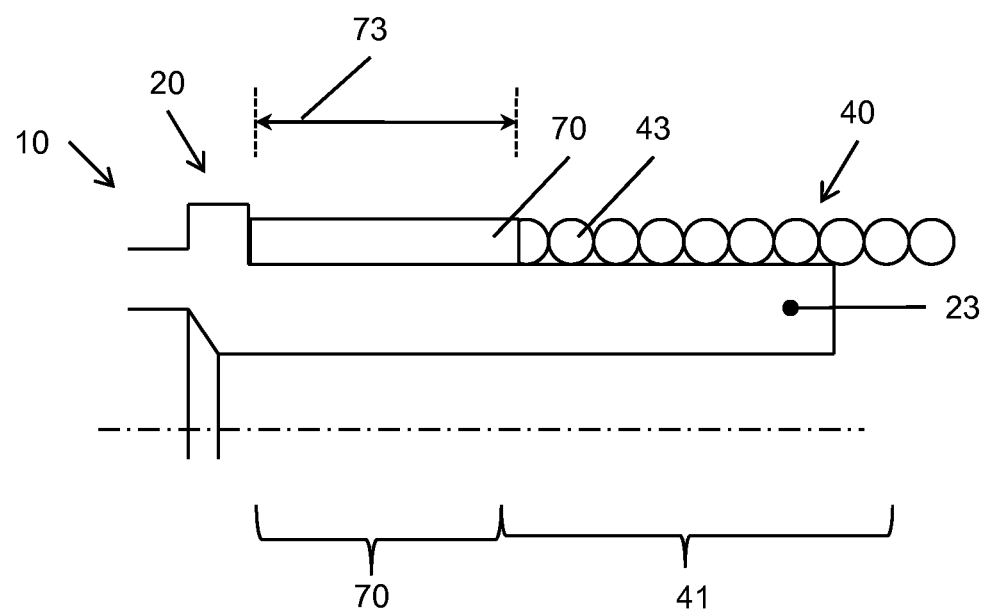
FIG. 9 illustrates an alternative embodiment option of the medical electrode system.

The joined medical electrode system 10 is illustrated in FIGS. 7 to 9. A sectional enlargement of a stimulation electrode 20, which is embodied according to one embodiment and including a conduction coil 40, is illustrated in each case. The sectional enlargement thereby includes that area of the stimulation electrode 20, which is characterized in FIG. 1 by means of the character I. To attain the illustrated connection situation of the conduction coil 40 with the stimulation electrode 20, provision is made according to one embodiment for:

a. at least one from the group of an inner diameter 72 of a connection element 70 of the conduction coil 40 and of an outer diameter 27 of an end area 23 of the stimulation electrode 20 to be changed by means of a thermal impact, b. the connection element 70 to be slid onto the end area 23 and c. the connection element 70 to be shrink-fitted onto the end area 23 by reaching a thermal balance.

A difference between the outer radius 27 and the inner radius 72 of the connection element 70 is attained by means of the thermal impact, for example, the heating of the connection element 70 or the cooling of the end area 23. It is thus possible to slide the connection element 70 onto the end area 23. This is to because the inner diameter 72 should be maximally the same as the outer diameter 27 of the end area 23 of the stimulation electrode in response to the thermal balance between conduction coil 40 and stimulation electrode 20.

FIGS. 7 and 9 clarify how the medical electrode system 10 is formed when the connection element 70 is formed from a plurality of loops 43, which are connected by means of welding points 80. FIG. 9, however, illustrates the medical electrode system, in the case of which the connection element 70 is formed by means of a tube-like, one-piece element. In the illustrated exemplary embodiment, a length 73 of the connection element 70 is chosen to be shorter than a length 24 of the end area 23 (see FIG. 1). A first part of the conduction area 41 thus still attains a guiding through the end area 23 of the stimulation electrode. The conduction coil 40 introduces possible bending and shearing forces into the stimulation electrode 20 in the area of an end 85. The area by area guiding of the conduction area 41 through parts of the end area 23 prevents that the shearing forces act on the connection of conduction coil 40 and connection element 70 by means of material engagement. This further increases the durability of the medical electrode system including the connection of conduction coil and stimulation electrode 20 according to one embodiment.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A medical electrode system comprising:
a conduction coil; and
a stimulation electrode;
wherein the stimulation electrode encompasses a base body comprising a top area and an end area;
characterized in that the conduction coil encompasses a connection element;
wherein the connection element is assembled from a plurality of loops of the conduction coil through which electrical pulses are transmitted by an implantable medical apparatus; and
wherein the connection element is directly thermally shrink-fitted onto the end area thereby creating a positive connection therewith and the difference of melting temperatures of the connection element and the end area is at least 1000° C.

2. The medical electrode system according to a to claim 1, characterized in that an inner diameter of the connection element is adapted to an outer diameter of the end area, so as to thermally shrink-fit the conduction coil onto the stimulation electrode in a connection situation.

3. The medical electrode system according to claim 1, characterized in that the conduction coil and/or the connection element encompasses MP-35.

4. The medical electrode system according to claim 1, characterized in that the end area and/or the connection element are embodied in a cylindrical manner.

5. The medical electrode system according to claim 1, characterized in that the connection element enters into a non-positive and/or positive connection with the stimulation electrode.

6. A method for producing a medical electrode system according to claim 1, including connecting a conduction coil to a stimulation electrode, comprising:
  changing by means of a thermal impact at least one from the group comprising an inner diameter of a connection element, of the conduction coil, and of an outer diameter of an end area of the stimulation electrode;
  sliding the connection element onto the end area; and
  shrink-fitting the connection element onto the end area by reaching a thermal balance.

7. The method according to claim 6, characterized in that a plurality of loops of the conduction coil are welded to one another, at least in part, for forming the connection element.

8. A method for connecting a conduction coil to a stimulation electrode, the method comprising:
  assembling a connection element from a plurality of loops of the conduction coil, the connection element having a melting temperature;
  heating an inner diameter of the connection element of the conduction coil;
  sliding the connection element onto an outer diameter of an end area of the stimulation electrode, the stimulation electrode having a melting temperature; and
  cooling the connection element so as to shrink-fit the connection element directly onto the end area thereby creating a positive connection between the connection element and the end area;
  characterized in that the melting temperature of the connection element is at least 1000° C. lower that the melting temperature of the stimulation electrode.

9. The method according to claim 6, further comprising welding a plurality of loops of the conduction coil to one another, at least in part, for forming the connection element.

10. The medical electrode system according to claim 1, wherein the difference of melting temperatures of the connection element and the end area is at least 1500° C.

11. The medical electrode system according to claim 1, wherein the melting temperature the end area is at least 2400° C.

12. The method of claim 8, wherein the difference of melting temperatures of the connection element and the end area is at least 1500° C.

13. The method of claim 8, wherein the melting temperature the end area is at least 2400° C.

* * * * *